(12) United States Patent
Boehlendorf et al.

(10) Patent No.: US 8,993,037 B2
(45) Date of Patent: Mar. 31, 2015

(54) DIHYDROCHALCONE PURIFICATION PROCESS

(75) Inventors: Bettina Boehlendorf, Rheinfelden (DE); Hubert Hug, Schliengen-Niedereggenen (DE); Judith Kammerer, Bad Boll (DE); Claus Kilpert, Mannheim (DE); Reinhold Carle, Altenriet (DE)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 13/981,176

(22) PCT Filed: Jan. 19, 2012

(86) PCT No.: PCT/EP2012/050756
§ 371 (c)(1),
(2), (4) Date: Jul. 23, 2013

(87) PCT Pub. No.: WO2012/104145
PCT Pub. Date: Aug. 9, 2012

(65) Prior Publication Data
US 2013/0302504 A1 Nov. 14, 2013

(30) Foreign Application Priority Data
Jan. 31, 2011 (EP) .................................. 11152766

(51) Int. Cl.
*A23L 1/30* (2006.01)
*C07H 15/20* (2006.01)
*C07H 1/08* (2006.01)
*C07H 15/203* (2006.01)

(52) U.S. Cl.
CPC ................. *C07H 15/20* (2013.01); *C07H 1/08* (2013.01); *C07H 15/203* (2013.01)
USPC ............ 426/638; 426/429; 426/431; 426/531

(58) Field of Classification Search
USPC .......................................................... 426/648
See application file for complete search history.

(56) References Cited

U.S. PATENT DOCUMENTS

2008/0096825 A1 4/2008 Ehrenkranz

FOREIGN PATENT DOCUMENTS

WO WO 2007/124102 11/2007

OTHER PUBLICATIONS

Tomds-Barberdn: Dihydrochalcones from apple juices and jams; Food Chemistry 46 (1993) 33-36, Feb. 1992.*
Schieber: A new process for the combined recovery of pectin and phenolic compounds from apple pomace; Innovative Food Science and Emerging Technologies 4 (2003) 99-107.*
Araújo: Vanillin production from lignin oxidation in a batch reactor; Chemical Engineering Research and Design 8 8 (2010) 1024-1032.*
International Search Report for PCT/EP2012/050756 mailed Mar. 6, 2012.

* cited by examiner

*Primary Examiner* — Patricia George
(74) *Attorney, Agent, or Firm* — Nixon & Vanderhye P.C.

(57) ABSTRACT

The present invention relates to an improved process for the preparation of an extract enriched in dihydrochalcones, and more specifically enriched in phlorizin, starting from a dry polyphenolic fraction originating from industrial apple processing. The invention also relates to a dihydrochal-cone extract obtainable by this process, and to a food or a nutraceutical product comprising a dihydrochalcone extract of the present invention.

13 Claims, No Drawings

DIHYDROCHALCONE PURIFICATION PROCESS

This application is the U.S. national phase of International Application No. PCT/EP2012/050756 filed 19 Jan. 2012 which designated the U.S. and claims priority to EP 11152766.9 filed 31 Jan. 2011, the entire contents of each of which are hereby incorporated by reference.

The present invention relates to an improved process for the preparation of an extract enriched in dihydrochalcones, and more specifically enriched in phloridzin, starting from a dry polyphenolic fraction originating from industrial apple processing. The invention also relates to a dihydrochalcone extract obtainable by this process.

The growth of horticulture industries worldwide has generated huge quantities of fruit wastes. These residues are generally a good source of carbohydrates, proteins, vitamins, minerals, antioxidants, and other bioactive secondary metabolites. Apple fruits are extensively used in the food industry to produce different types of apple cakes, apple juices and ciders and generates in parallel large amounts of apple pomace, or apple skin waste streams both containing large amounts of nutritionally interesting metabolites. Apple pomace takes the form of a heterogeneous mixture of seeds, cores, stems, skin, and parenchyma. Apple pomace is one of the main sources of pectins, a common food gelling agent, and can also be used for biotechnological productions. In apples, phenolic compounds are present in various parts of the fruit and can be classified in several classes: hydroxycinnamic acid derivatives, monomeric and oligomeric flavan-3-ols, dihydrochalcones, flavonols etc. An efficient use of apple by-products is a growing topic that can be considered as a key process towards achieving profitability and/or sustainability in apple industry.

Phlorizin (glucose, 1-[2-(beta-D-glucopyranosyloxy)-4,6-dihydroxyphenyl]-3-(4-hydroxyphenyl)-1-propanone); CAS No.: 60-81-1 is a member of the dihydrochalcone class of organic compounds. It consists of a glucose moiety and two aromatic rings joined by an alkyl spacer. Phlorizin is a natural product, which has been found in, and isolated from various fruit trees, including the root, bark, shoots, leaves and fruits of apple trees, and from all parts of strawberry plants. Moreover, phlorizin is a known potent glucose uptake blocker (WO 2001/15706) which is used to treat non-pathological forms of obesity (EP 1 338 270).

Phlorizin and/or natural extracts enriched in phlorizin may be prepared by multiple extraction steps usually requiring a further expensive chromatographic step (WO 2007/124102; EP 1 243 586), or a selective enzymatic step (Will et al. LWT (2007), 40: 1344-1351). However, the purification technologies described in the prior art to date are relatively expensive, time consuming, and difficult to operate in industrial scale starting from an industrial waste stream since they all involve a chromatographic or enzymatic step.

Because of the continuously increasing demand for phlorizin on the market, the object of the present invention was to provide a process for the preparation of phlorizin which is easy to carry out and affords economic advantages as a result of high yields. Furthermore, the process of the present invention yields a clearer product which is more stable and contains very low amounts of unwanted ortho-dihydroxy phenol structures e.g: quercetin and derivatives thereof, flavonols, flavanols, and hydroxycinnamic acids. This is particularly important because minor amounts of quercetin and derivatives thereof in a phlorizin preparation tend to oxidize during storage, thereby making the phlorizin preparation to turn brown which is unwanted for use in food formulations.

Surprisingly, it has been found that the process of the present invention delivers higher dihydrochalcone yields and less ortho-dihydroxy phenol structures at a very low processing cost compared to the use of other technologies. Furthermore, the process of the present invention only involves extraction and selective precipitation of unwanted side-products, making this process significantly more cost effective compared to any process of the prior art.

Thus, the present invention provides a process for the preparation of an extract enriched in dihydrochalcones and derivatives thereof, wherein said process comprising the steps of:
  (a) extracting a dried polyphenol extract with a food grade solvent,
  (b) alkalinising the extract from (a),
  (c) oxidizing the resulting solution from (b),
  (d) filtering or centrifugating the mixture of (c),
  (e) optionally, evaporating the resulting solution of (d) to remove residual solvent, and solubilising the dried material in water
  (f) drying the resulting extract.

Dihydrochalcones and derivatives thereof, means any compound selected from: phloridzin, phloretin, phloretin-2'-O-β-D-xylopyranosyl-(1-6)-β-D-glucopyranoside, and other phloretin glycosides.

In a particular embodiment, the raw material used as starting material is a dried polyphenol extract derived from industrial apple processing. It is to be understood by the word apple, domestic and wild apple. The raw material may be apple pomace as a residue from apple juice or cider production, or a further purified polyphenolic extract derived from apple pomace, or apple skin. More preferably, the raw material used as starting material is a dried polyphenol extract derived from the apple pectin production process. Even more preferred, is a dried polyphenol extract resulting from the pectin production process as described in WO 2001/78859. Furthermore, when the dried polyphenol extract is derived from industrial apple processing, it preferably comprises at least 1, preferably at least 5, more preferably at least 8 weight-% phlorizin. It may also comprise up to 5% quercetin and derivatives thereof.

In another embodiment, the extraction step (step (a)) of the process according to the present invention is performed with a pure food grade solvent, with water or with a water-solvent mixture. The water-solvent mixture comprises from 1 up to 99 volume-% water, preferably up to 50, more preferably up to 30, even more preferably up to 10 volume-% water. Preferred food grade solvent according to the present invention is selected from: propane, butane, pentane, hexane, cyclohexane, heptane, methanol, ethanol, butan-1-ol, butan-2-ol, 3-methyl-1-butanol, propan-1-ol, 2-methyl-1-propanol, isopropanol, 1-pentanol, methyl acetate, ethyl acetate, ethyl formate, butyl acetate, isobutyl acetate, propyl acetate, isopropyl acetate, acetone, ethylmethylketone, methylisobutyl ketone, dichloro methane, ethyl ether, diethyl ether, tert-butylmethylether, 1,1,1,2-tetrafluoroethane, anisole, cumene.

In a further embodiment, the extraction solvent of step (a) is selected from: methanol, ethanol, and isopropanol. Even more preferred food grade extraction solvent is 100% isopropanol in view of its efficiency in extracting phlorizin and selectivity against extraction of quercetin and derivatives thereof.

To ensure a high yield, and a rapid extraction process, it is critical that the extraction step according to the present invention (step (a)) is as efficient as possible. Therefore, in another embodiment, the dried polyphenol extract following the addition of the solvent is treated with ultrasound until complete solubilisation or dispersion of particles. In a preferred embodiment, an amount of 100 to 1000 Watts of ultrasounds is applied in a 10 litre water bath. Then, the extraction is best performed according to standard procedures known to the person skilled in the art. It can be performed by any conventional means to introduce shear forces into the extract-solvent mixture adjusting the extraction time depending on the temperature and pressure applied. In a preferred embodiment, the extraction is performed with mixing for at least 10 minutes at ambient temperature (between 18° C. to 25° C.).

In a further embodiment, the extraction process of step (a) is performed with a ratio of solvent to dried polyphenol extract comprised between 500/1 and 10/1 litre/kilogram, preferably between 500/1 and 50/1 litre/kilogram, more preferably between 300/1 and 80/1 litre/kilogram.

In a further embodiment, the alkalinising step (b) is performed by addition of a base until pH is comprised between pH 7 and pH 14, preferably comprised between pH 8 and pH 14, even more preferably comprised between pH 9 and pH 14. For this alkalinising step any strong base having a $pK_b$ smaller than 4.5, preferably smaller than 2 can be used. Preferably sodium hydroxide (NaOH) is used in a concentration as high as possible as to avoid adding large amounts of aqueous alkaline solution to the extraction solvent. Optionally, the alkalinising step can be performed in the same conditions at the start of the extraction process.

In a further embodiment, the oxidizing step (step (c)) is performed by bubbling atmospheric air into the alkalinised extract of step (b). The extent of the oxidation is adjusted depending on the volume of solvent and the amount of polyphenols. In a preferred embodiment, 10 to 80 litres of air are bubbled per 100 ml of solvent containing 1 g dried polyphenol extract. The extent of oxidation is best controlled by HPLC by measurement of the complete oxidation of the orthodihydroxy phenolic structures.

In a further embodiment, at the end of the oxidation process of step (c), a protein is added to the oxidation solution, wherein the protein is positively charged at the pH of the oxidation solution. The positively charged protein acts as a powerful fining agent. Any positively charged protein may be used, but in a preferred embodiment, gelatine is used. The concentration of the positively charged protein is to be optimized depending on the composition of the oxidation solution according to standard fining procedures.

In a further embodiment, a lysine and/or cystein rich protein is added to the oxidation solution. Preferred lysine and/or cystein rich protein are proteins of plant origin. In particular embodiments, the lysine and or cystein rich protein contains at least 8% amino acids represented by lysine and cystein, preferably at least 10%, 12%, 14%, 16%, 18%, 20%, or at least 22%.

In a further embodiment, when proteins are added, the pH of the oxidized solution is adjusted at the end of the reaction to the isoelectric point of the above mentioned protein using an acid or a base.

The filtering or centrifugating step (d) is performed according to standard procedures in order to remove any non solubilised particles. The resulting supernatant is then optionally submitted to evaporation of the solvent. This can be performed by any standard evaporation technology. The drying step (f) can be performed by lyophilisation or spray drying according to standard procedures.

The present invention also provides a dihydrochalcone extract obtainable by the process of the invention. In a preferred embodiment, the dihydrochalcone extract comprises less than 1 wt-% ortho-dihydroxy phenol structures. More preferably, it comprises less than 0.5 wt-% quercetin and/or derivatives thereof.

In a preferred embodiment, the dihydrochalcone extract according to the present invention comprises more than 10% dihydrochalcones and less than 1 wt-% quercetin and/or derivatives thereof, more preferably less than 0.5 wt-% quercetin and/or derivatives thereof.

The invention also provides a food or a nutraceutical product comprising a dihydrochalcone extract according to the present invention.

The invention is further illustrated by the following examples.

EXAMPLES

Example 1

Enrichment of Dihydrochalcones, Especially of Phlorizin, from a Polyphenol Extract In this experiment, amounts of 0.5 g (±0.0025 g) of polyphenols extract (Herbstreith & Fox; Neuenbürg, DE) were stirred with 50 ml of ethanol in 100 ml screw cap glass flasks for 30 minutes at 300 rpm in a water bath, and the samples were exposed to ultrasound within the initial 30 seconds. All experiments were performed in quadruplicate.

For UPLC-DAD/MS analyses aliquots of 2 ml were centrifuged (3 minutes at 13.2000 rpm) and subsequently diluted 1:6 (v:v) with methanol/water (1:1, v:v). The remainder was adjusted to a pH value of 11 by adding NaOH, and subsequently aliquots of 2 ml were withdrawn for UPLC-DAD/MS analysis. Afterwards, the basic extracts were oxidized for 15 minutes by bubbling air at a flow of 1.3 litre/minute, and the precipitates were separated by centrifugation (3220 rcf, for 15 minutes). The supernatants were transferred in 50 ml volumetric flasks and made up with ethanol. Aliquots of 200 µl of these solutions were withdrawn for UPLC-DAD/MS analyses. Furthermore, ethanol was removed using a rotary evaporator at 30° C., and the residue was quantified gravimetrically.

In addition, all samples were lyophilized. For this purpose, 5 ml of water was added to the samples dried by rotary evaporation for dissolving them prior to their freezing in an isopropanol-dry ice mixture followed by lyophilization.

Based on the phlorizin contents of the ethanol extracts prior to and after oxidation quantified by UPLC-DAD/MS at $\lambda_{max}$=285 nm the phlorizin amounts of the lyophilisate as well as its proportion in the lyophilisate were calculated (Table 1). Furthermore, the decrease of quercetin contents and of its derivatives during the process has been monitored by UPLC-DAD/MS at $\lambda_{max}$=370 nm.

TABLE 1

Phlorizin enrichment during the process (mean values of quadruplicates)

| Sample Description | Amount of starting extract (g) | Phlorizin concentration of extract (g/l) | mg phloridzin/ 50 ml extract | Phlorizin content of the extract (%) |
|---|---|---|---|---|
| Post extraction | 0.5011 | 0.93 | 46.6 | 9.3 |
| Post NaOH addition | 0.5011 | 0.86 | 43.3 | 8.6 |
| Post oxidation | 0.5011 | 0.76 | 38.0 | 7.6 |

Following lyophilisation, the extract weight (average of 4 experiments) was 256 mg. The lyophilisate contained 14.9 weight % phlorizin, and 203 mg non-phlorizin compounds.

Example 2

Enrichment of Dihydrochalcones, Especially of Phlorizin, from a Polyphenol Extract In this experiment, amounts of 0.5 g (±0.0025 g) of polyphenols extract (Herbstreith & Fox; Neuenbürg, DE) were stirred with 50 ml of isopropanol in 100 ml screw cap glass flasks for 30 minutes at 300 rpm in a water bath, and the samples were exposed to ultrasound within the initial 30 seconds. All experiments were performed in quadruplicate.

For UPLC-DAD/MS analyses aliquots of 2 ml were centrifuged (3 minutes at 13.2000 rpm) and subsequently diluted 1:6 (v:v) with methanol/water (1:1, v:v). The remainder was adjusted to a pH value between 10.50 and 10.98 by adding 1.1 ml of 1M NaOH, and subsequently aliquots of 2 ml were withdrawn for UPLC-DAD/MS analysis. Afterwards, the basic extracts were oxidized for 15 minutes by bubbling air at a flow of 1.3 litre/minute, and the precipitates were separated by centrifugation (3220 rcf, for 15 minutes). The supernatants were transferred in 50 ml volumetric flasks and made up with isopropanol. Aliquots of 200 µl of these solutions were withdrawn for UPLC-DAD/MS analyses. Furthermore, isopropanol was removed using a rotary evaporator at 30° C., and the residue was quantified gravimetrically.

In addition, all samples were lyophilized. For this purpose, 5 ml of water was added to the samples dried by rotary evaporation for dissolving them prior to their freezing in an isopropanol-dry ice mixture followed by lyophilization.

Based on the phlorizin contents of the isopropanol extracts prior to and after oxidation quantified by UPLC-DAD/MS at $\lambda_{max}=285$ nm the phlorizin amounts of the lyophilisate as well as its proportion in the lyophilisate were calculated (Table 1). Furthermore, the decrease of quercetin contents and of its derivatives during the process has been monitored by UPLC-DAD/MS at $\lambda A_{max}=370$ nm.

Amount of quercetin and derivatives thereof in the dried polyphenol extract: 10 mg Amount of quercetin and derivatives thereof in the purified product: less than 0.2 mg

TABLE 2

Phlorizin enrichment during the process (mean values of quadruplicates)

| Sample Description | Amount of starting extract (g) | Phlorizin concentration of extract (g/l) | mg phlorizin/ 50 ml extract | Phlorizin content of the extract (%) |
|---|---|---|---|---|
| Post extraction | 0.5012 | 1.05 | 52.4 | 10.5 |
| Post NaOH addition | 0.5012 | 0.63 | 31.4 | 6.3 |
| Post oxidation | 0.5012 | 0.55 | 27.4 | 5.5 |

Following the oxidation and lyophilisation, the extract weight (average of 4 experiments) was 111.7 mg. The lyophilisate contained 24.5 weight % phloridzin.

The invention claimed is:

1. A process for the preparation of an extract comprising dihydrochalcones and derivatives thereof, wherein said process comprises the steps of:
   (a) extracting with a food grade solvent a dried polyphenol extract comprising dihydrochalcones and derivatives thereof obtained from apple pomace,
   (b) alkalinising the food grade solvent with extract from (a) to form a solution,
   (c) oxidizing the resulting solution from (b) to form a mixture,
   (d) filtering or centrifugating the mixture of (c) to form an extract,
   (e) optionally, evaporating the resulting extract of (d) to remove residual solvent, and/or solubilising the dried material thereof in water, and
   (f) drying the extract comprising dihydrochalcones and derivatives thereof.

2. The process according to claim 1, wherein the dried polyphenol extract is derived from an industrial apple processing.

3. The process according to claim 1, wherein the dried polyphenol extract is derived from an apple pectin production process.

4. The process according to claim 1, wherein step (a) is performed with a pure food grade solvent, with water, or with a water-solvent mixture.

5. The process according to claim 4, wherein the solvent is selected from the group consisting of propane, butane, pentane, hexane, cyclohexane, heptane, methanol, ethanol, butan-1-ol, butan-2-ol, 3-methyl-1-butanol, propan-1-ol, 2-methyl-1-propanol, isopropanol, 1-pentanol, methyl acetate, ethyl acetate, ethyl formate, butyl acetate, isobutyl acetate, propyl acetate, isopropyl acetate, acetone, ethylmethylketone, methylisobutyl ketone, di-chloro methane, ethyl ether, diethyl ether, tert-butylmethylether, 1,1, 1,2- tetrafluoroethane, and anisole, cumene.

6. The process according to claim 4, wherein the solvent used in step (a) is selected from the group consisting of methanol, ethanol, and isopropanol.

7. The process according to claim 1, wherein a ratio of solvent to dried polyphenol extract in step (a) is between 500/1 and 10/1 liter/Kg.

8. The process according to claim 1, wherein the alkalinisation of step (b) comprising adding a base until the solution has a pH between pH7 and pH14.

9. The process according to claim 1, wherein the oxidation step (c) comprises bubbling atmospheric air into the solution.

10. The process according to claim 1, wherein step (c) comprises adding a protein to the oxidation solution as a fining agent, wherein the protein is positively charged at the pH of the oxidation solution.

11. The process according to claim 1, wherein step (c) comprises adding a lysine and/or cystein rich protein to the oxidation solution.

12. The process according to claim 10, wherein step (c) comprises adjusting the pH of the oxidized solution to an isoelectric point of the protein.

13. The process according to claim 1, wherein the drying step (f) is performed by spray drying.

* * * * *